US010654876B2

(12) United States Patent
Duan et al.

(10) Patent No.: US 10,654,876 B2
(45) Date of Patent: May 19, 2020

(54) TH-302 SOLID FORMS AND METHODS RELATED THERETO

(71) Applicant: Molecular Templates, Inc., Austin, TX (US)

(72) Inventors: Jian-Xin Duan, South San Francisco, CA (US); Mark Matteucci, Portola Valley, CA (US); Nipun Davar, Pleasanton, CA (US); Denise Andersen, Montara, CA (US)

(73) Assignee: Molecular Templates, Inc., Austin, TX (US)

( * ) Notice: Subject to any disclaimer, the term of this patent is extended or adjusted under 35 U.S.C. 154(b) by 0 days.

(21) Appl. No.: 16/193,160

(22) Filed: Nov. 16, 2018

(65) Prior Publication Data

US 2019/0127404 A1    May 2, 2019

Related U.S. Application Data

(62) Division of application No. 15/326,990, filed as application No. PCT/US2015/040642 on Jul. 15, 2015, now Pat. No. 10,131,683.

(60) Provisional application No. 62/025,956, filed on Jul. 17, 2014.

(51) Int. Cl.
*C07F 9/6506* (2006.01)
*A61K 31/661* (2006.01)
*A61K 31/664* (2006.01)
*A61K 45/06* (2006.01)
*A61K 31/675* (2006.01)

(52) U.S. Cl.
CPC .......... *C07F 9/6506* (2013.01); *A61K 31/664* (2013.01); *A61K 31/675* (2013.01); *A61K 45/06* (2013.01); *C07B 2200/13* (2013.01)

(58) Field of Classification Search
CPC .......................... C07F 9/6506; A61K 31/661
See application file for complete search history.

(56) References Cited

U.S. PATENT DOCUMENTS

| | | | |
|---|---|---|---|
| 5,472,956 | A | 12/1995 | Borch et al. |
| 6,482,953 | B1 | 11/2002 | Kim et al. |
| 8,507,464 | B2 | 8/2013 | Matteucci et al. |
| 2004/0214798 | A1 | 10/2004 | Hu |
| 2008/0269268 | A1 | 10/2008 | Schirok et al. |
| 2010/0256139 | A1 | 10/2010 | Rockway et al. |
| 2011/0251159 | A1 | 10/2011 | Matteucci et al. |
| 2014/0010805 | A1 | 1/2014 | Hart et al. |
| 2014/0170240 | A1 | 6/2014 | Matteucci et al. |
| 2018/0044360 | A1 | 2/2018 | Duan et al. |

FOREIGN PATENT DOCUMENTS

| | | |
|---|---|---|
| CN | 102924507 A | 2/2013 |
| JP | 2018-513876 A | 5/2018 |
| WO | WO-2004/087075 | 10/2004 |
| WO | WO-2006/057946 A2 | 6/2006 |
| WO | WO-2007/002931 A2 | 1/2007 |
| WO | WO-2007/098089 A2 | 8/2007 |
| WO | WO-2008/083101 A1 | 7/2008 |
| WO | WO-2008/151253 A1 | 12/2008 |
| WO | WO-2009/018163 A1 | 2/2009 |
| WO | WO-2010/044686 A1 | 4/2010 |
| WO | WO-2010/048330 A1 | 4/2010 |
| WO | WO-2011/066416 A1 | 6/2011 |
| WO | WO-2014/131023 A1 | 8/2014 |
| WO | WO-2015/051921 A1 | 4/2015 |
| WO | WO-2016/145092 A1 | 9/2016 |
| WO | WO-2016/161342 A2 | 10/2016 |
| WO | WO-2016/210175 A1 | 12/2016 |
| WO | WO-2017/087428 A1 | 5/2017 |

OTHER PUBLICATIONS

Chen, Y. et al., "Design of anticancer prodrugs for reductive activation", Medicinal Research Reviews, vol. 29, No. 1, 2009, pp. 29-64.
Duan, J-X. et al. (2008) "Potent and Highly Selective Hypoxia-Activated Achiral Phosphoramidate Mustards as Anticancer Drugs," J. Med Chem 51:2412-2420.
Extended European Search Report issued in 16774352.5 dated Nov. 6, 2018, 11 pages.
Extended European Search Report issued in 16815334.4 dated Dec. 21, 2018, 7 pages.
Golub, T.R. et al. (1999) "Molecular Classification of Cancer: Class Discovery and Class Prediction by Gene Expression Monitoring," Science 286:531-537.
Guise, C.P. et al. (2014) "Bioreductive prodrugs as cancer therapeutics: targeting tumor hypoxia," Chinese Journal of Cancer 33(2):80-86.
Hay et al. Substituent effects on the kinetics of reductively-initiated fragmentation of nitrobenzyl carbamates designed as triggers for bioreductive prodrugs, J. Chem. Soc., Perkin Trans. 1, 1999, 2759-2770. (Year:1999).
International Application No. PCT/US2015/040642, International Preliminary Report on Patentability dated Jan. 26, 2017, 7 pages.
International Application No. PCT/US2015/040642, International Search Report and Written Opinion dated Sep. 29, 2015, 9 pages.
International Preliminary Report on Patentability issued in PCT/US2016/039092 dated Jan. 4, 2018, 9 pages.
International Search Report and Written Opinion (ISA/KR) for International Application No. PCT/US2016/039092, dated Sep. 6, 2016.
Jain, M. et al. (2004) "Sulfonyl-containing aldophosphamide analogues as novel anticancer prodrugs targeted against cyclophosphamide-resistant tumor cell lines," Journal of Medicinal Chemistry 47(15):3843-3852.

(Continued)

*Primary Examiner* — Karen Cheng
(74) *Attorney, Agent, or Firm* — Foley & Lardner LLP; Daniel R. Shelton; Yogeeta B. Jadhav

(57) ABSTRACT

The present invention provides a new method for making TH-302 and solid forms thereof. The compound in its solid form is an effective anti-cancer agent and may be used in various pharmaceutical compositions, and are particularly effective for the treatment of cancer. The invention also provides a method for preparing such compounds and forms and for treating cancer in a mammal comprising the step of administering a therapeutically effective amount of a solid form of TH-302 thereof.

18 Claims, 5 Drawing Sheets

(56) References Cited

OTHER PUBLICATIONS

K. Misiura et al., "Sterospecific synthesis of chiral metabolites of Itostamide and their determination in the Urine", Journal of Medicinal Chemistry., vol. 26, 1983, pp. 674-679, XP002786859, USAmerican Chemical Society. Washington. ISSN: 0022-2623.

Li, Z. et al., "Nitrobenzocyclophosphamides as Potential Prodrugs for Bioreductive Activation: Synthesis, Stability, Enzymatic Reduction, and Antiproliferative Activity in Cell Culture", Bioorganic & Medicinal Chemistry, vol. 11, No. 19, 2003, pp. 4171-4178.

Mulcahy, R.T. et al. (1994) "Nitrobenzyl phosphorodiamidates as potential hypoxia-selective alkylating agents", Journal of Medicinal Chemistry 37:1610-1615.

NIH National Cancer Institute (2015) "Targeted Cancer Therapies Fact Sheet," see http://www.cancer.gov/about-cancer/treatment/types/targeted-therapies/targeted-therapies-fact-sheet, accessed Dec. 8, 2015.

Non-Final Office Action in U.S. Appl. No. 15/326,990, dated Apr. 30, 2018.

Non-Final Office Action in U.S. Appl. No. 15/557,053, dated Jun. 22, 2018.

Non-Final Office Action on U.S. Appl. No. 15/563,481 dated Nov. 16, 2018.

Non-Final Office Action on U.S. Appl. No. 15/736,285 dated Sep. 27, 2018.

Non-Final Office Action on U.S. Appl. No. 15/752,854 dated Nov. 20, 2018.

Notice of Allowance in U.S. Appl. No. 15/326,990, dated Jul. 5, 2018.

Notice of Allowance on U.S. Appl. No. 15/326,990 dated Oct. 15, 2018.

Notice of Allowance on U.S. Appl. No. 15/736,285 dated Jan. 24, 2019.

Rastelli et al. Discovery of New Inhibitors of Aldose Reductase from Molecular Docking and Database Screening. Bioorganic & Medicinal Chemistry 10 (2002) 1437-1450. (Year: 2002).

Restriction Requirement in U.S. Appl. No. 15/563,481, dated Jul. 25, 2018.

Extended European search report issued in 16762438.6 dated Jul. 3, 2018, 10 pages.

Final Office Action on U.S. Appl. No. 15/563,481 dated Apr. 22, 2019.

Hu et al., "Synthesis and structure-activity relationships of nitrobenzyl phosphoramide mustards as nitroreductase-activated prodrugs", Bioorganic & Medicinal Chemistry Letters 21 (2011) 3986-3991.

International Search Report and Written Opinion (ISA/KR) for International Application No. PCT/US2016/062114, dated Mar. 9, 2017.

International Search Report and Written Opinion (ISA/US) for International Application No. PCT/US2016/021581, dated Jun. 2, 2016.

International Search Report and Written Opinion (ISA/US) for International Application No. PCT/US2016/025665, dated Sep. 8, 2016.

Notice of Allowance on U.S. Appl. No. 15/557,053 dated Apr. 22, 2019.

Notice of Allowance on U.S. Appl. No. 15/557,053 dated May 15, 2019.

Notice of Allowance on U.S. Appl. No. 15/557,053 dated Dec. 28, 2018.

Notice of Allowance on U.S. Appl. No. 15/752,854 dated Apr. 25, 2019.

Notice of Allowance on U.S. Appl. No. 16/392,477 dated Jan. 30, 2020, 9 pages.

$^1$H NMR of TH-302 (Form A)

XRPD of TH-302 (Form A) showing peak information

| Angle | d value | Intensity | Intensity % |
|---|---|---|---|
| 2-Theta ° | Angstrom | Count | % |
| 10.637 | 8.31011 | 74.1 | 57 |
| 10.95 | 8.07346 | 25 | 19.2 |
| 13.716 | 6.45113 | 88.2 | 67.9 |
| 14.118 | 6.26801 | 40.6 | 31.2 |
| 15.239 | 5.80948 | 36.4 | 28 |
| 17.386 | 5.09673 | 72.5 | 55.8 |
| 17.829 | 4.97106 | 108 | 83.2 |
| 18.209 | 4.86799 | 83.3 | 64.1 |
| 18.477 | 4.798 | 35.1 | 27 |
| 19.351 | 4.58329 | 124 | 95.8 |
| 20.434 | 4.34272 | 36.4 | 28 |
| 21.141 | 4.19901 | 90.3 | 69.5 |
| 21.452 | 4.13883 | 26.3 | 20.3 |
| 22.388 | 3.96793 | 102 | 78.3 |
| 23.164 | 3.83678 | 70.1 | 53.9 |
| 23.585 | 3.76923 | 22.6 | 17.4 |
| 24.27 | 3.66433 | 37 | 28.5 |
| 24.57 | 3.62024 | 36.4 | 28 |
| 25.008 | 3.55781 | 34.4 | 26.5 |
| 25.892 | 3.43831 | 70.1 | 54 |
| 26.23 | 3.39483 | 130 | 100 |
| 27.169 | 3.27956 | 62.3 | 47.9 |
| 27.523 | 3.23821 | 29.6 | 22.8 |
| 27.764 | 3.21058 | 33.4 | 25.7 |
| 28.26 | 3.15538 | 45.9 | 35.3 |
| 28.429 | 3.13697 | 56.7 | 43.6 |
| 28.807 | 3.09669 | 28.6 | 22 |
| 29.179 | 3.05803 | 102 | 78.1 |
| 33.395 | 2.68097 | 30.2 | 23.2 |
| 34.341 | 2.60929 | 31.5 | 24.3 |
| 35.236 | 2.54501 | 50.8 | 39.1 |
| 36.697 | 2.44699 | 22.9 | 17.6 |
| 37.504 | 2.39615 | 24.8 | 19.1 |
| 39.776 | 2.2644 | 25.1 | 19.4 |
| 40.146 | 2.24435 | 24.4 | 18.8 |
| 40.587 | 2.22099 | 25.8 | 19.8 |
| 41.431 | 2.17767 | 26.2 | 20.2 |
| 45.798 | 1.97967 | 24.8 | 19.1 |
| 46.71 | 1.94309 | 23.7 | 18.2 |
| 47.752 | 1.9031 | 25.4 | 19.6 |
| 48.394 | 1.87934 | 27.4 | 21.1 |

Peak listing of XRPD data of TH-302 (Form A)

*FIG. 4*

TH-302 SOLID FORMS AND METHODS RELATED THERETO

CROSS REFERENCE TO RELATED APPLICATIONS

This application is a divisional of U.S. application Ser. No. 15/326,990, filed Jan. 17, 2017, which is a 371 U.S. national application of International Application No. PCT/US2015/040642, filed Jul. 15, 2015, which claims the benefit of and priority to U.S. Provisional Application No. 62/025,956, filed Jul. 17, 2014, all of which are hereby incorporated by reference herein in their entireties.

BACKGROUND OF THE INVENTION

Cancer is a major cause of death in the industrialized world for which new and more efficacious treatments are needed. Despite the existence of anti-cancer agents, there still exists a need for more effective anti-cancer agents. A promising new class of anti-cancer agents has emerged (see U.S. Pat. No. 7,550,496, incorporated herein by reference), and the most promising compound in that class, called TH-302 (see PCT Pub. Nos. WO 2007/002931; WO 2008/083101; and WO 2010/048330, each of which is incorporated herein by reference), is now in advanced clinical testing. Because of the dire prognosis for patients with cancer, further advancements in pharmaceutical management of the condition are needed.

In addition, while biological activity is a sine non qua for an effective drug, the compound must be capable of large scale manufacturing and the physical properties of the compound can markedly impact the effectiveness and cost of a formulated active ingredient. Amorphous and different crystalline solid/polymorphic forms of compounds are frequently encountered among pharmaceutically useful compounds. Polymorphism is the ability of any element or compound to crystallize as more than one distinct crystalline species. Physical properties including solubility, melting point/endotherm maximum, density, hardness, crystalline shape and stability can be quite different for different forms of the same chemical compound.

Crystalline solid and amorphous forms may be characterized by scattering techniques, e.g., x-ray diffraction powder pattern, by spectroscopic methods, e.g., infra-red, solid state $^{13}C$ and $^{19}F$ nuclear magnetic resonance spectroscopy and by thermal techniques, e.g., differential scanning calorimetry or differential thermal analysis. Although the intensities of peaks in the x-ray powder diffraction patterns of different batches of a compound may vary slightly, the peaks and the peak locations are characteristic for a specific crystalline solid or amorphous form. Additionally, infrared, Raman and thermal methods have been used to analyze and characterize crystalline and solid amorphous forms. Solid and amorphous forms may be characterized by data from the X-ray powder diffraction pattern determined in accordance with procedures which are known in the art (see J. Haleblian, J. Pharm. Sci. 1975 64:1269-1288, and J. Haleblain and W. McCrone, J. Pharm. Sci. 1969 58:911-929). Although the intensities of peaks in the x-ray powder diffraction patterns of different batches of the compounds may vary slightly, the peaks and the peak locations are characteristic for a specific crystalline solid form.

The problems which must be solved are to (i) identify a suitable manufacturing process to prepare, purify and recover the active compounds, (ii) provide an acceptable form of the compound which is soluble in pharmaceutically acceptable solvents, (iii) amenable to manipulation (e.g. flowability and particle size) and formulation with negligible decomposition or change of the physical and chemical characteristics of the compound, and (iv) exhibits acceptable chemical stability in the formulation. In addition, forms containing a high molar percent of the active ingredient are highly desirable since they minimize the quantity of material which must be formulated and administered to produce a therapeutically effective dose. These are often conflicting requirements making identification of suitable solid forms a challenging and important problem which must be solved by the skilled pharmaceutical scientist before drug development can proceed in earnest.

Therefore, there is a need for new methods of making compounds and crystalline solid forms of these compounds of the invention and an efficient process for producing the compounds and crystalline solid forms of the compounds of the invention. Solutions to the above difficulties and deficiencies are needed before compounds become effective for routine treatment of cancer.

Accordingly, efforts were made to discover other forms of compounds of the invention and to investigate the properties thereof. There were discovered crystalline solid forms of compounds of the invention. The present invention fulfills the above needs by providing polymorphs and methods for treating and preventing cancer, while presenting a better adverse effect profile.

SUMMARY OF THE INVENTION

In one aspect, the present invention provides compound the compound "TH-302" which refers to the compound of formula:

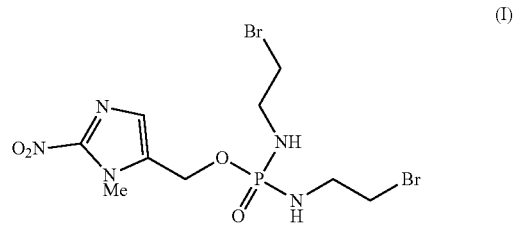 [SMILES: Cn1c(COP(=O)(NCCBr)NCCBr)cnc1[N+](=O)[O-]]

(I)

The invention also covers all pharmaceutically acceptable salts of the TH-302.

In another aspect, the invention provides crystalline solid forms of TH-302.

In another aspect, the invention provides pharmaceutical compositions for treating cancer in a mammal. The compositions contain a therapeutically effective amount of TH-302 or a pharmaceutically acceptable salt thereof and a pharmaceutically acceptable carrier or excipient. The invention further provides a method for preventing or treating cancer in a mammal by administering a therapeutically effective amount of TH-302 or a pharmaceutically acceptable salt thereof.

In still another aspect, the present invention provides methods for preparing TH-302, and its crystalline solid forms and pharmaceutical compositions for treating cancer and in a mammal.

BRIEF DESCRIPTION OF THE DRAWINGS

FIG. 4 shows XRPD peak information for crystalline solid form A of TH-302.

DETAILED DESCRIPTION OF THE INVENTION

Figure 1:
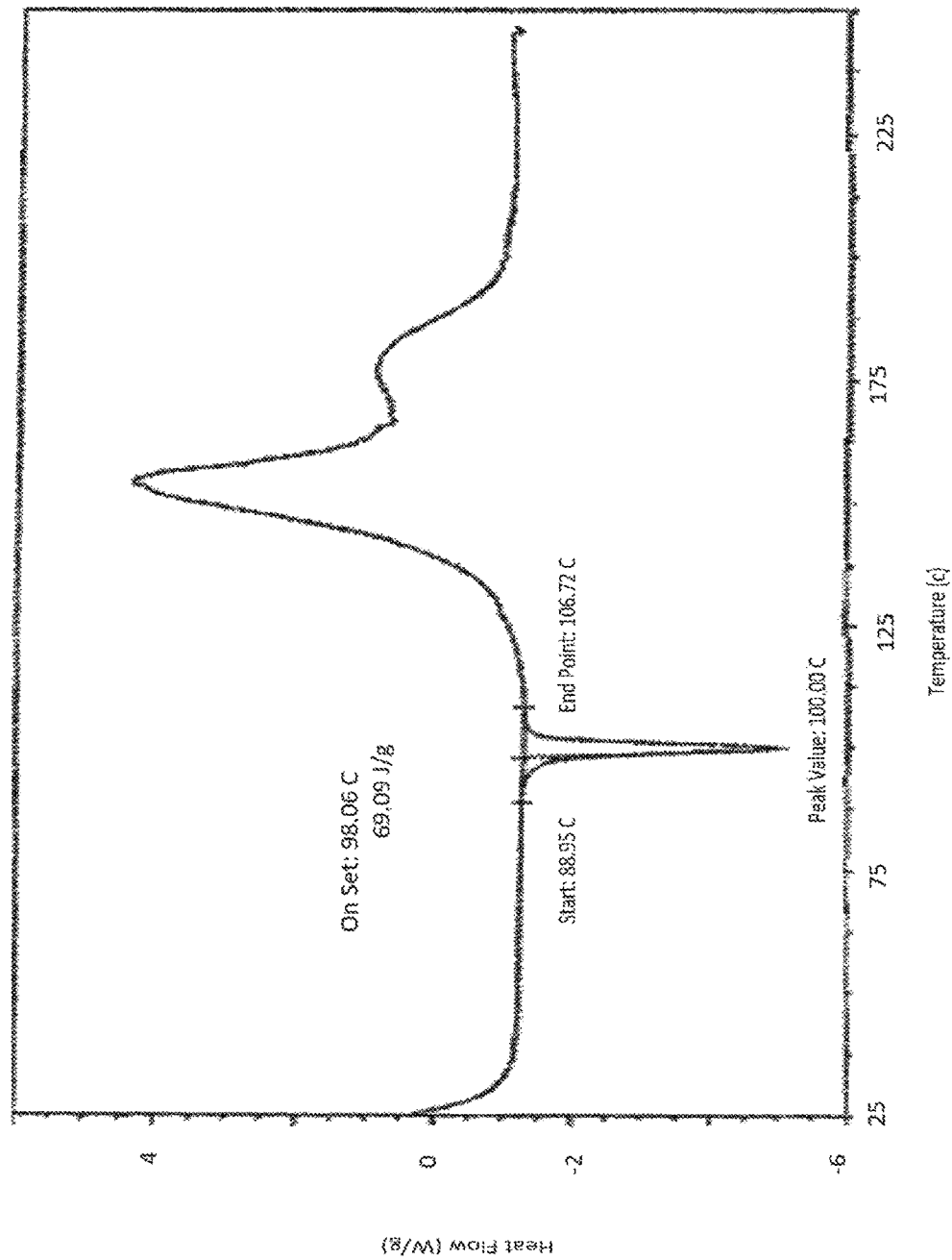
FIG. 1 provides the differential scanning calorimetry (DSC) data of crystalline solid form A of TH-302.

The practice of the present invention includes the use of conventional techniques of biochemistry, medicinal chemistry, pharmacology and immunology, which are within one of skill in the art.

The present invention involves TH-302 and crystalline solid forms thereof, and their preparation. TH-302 has excellent crystallinity, stability and purity. The compounds of the present invention are useful for the treatment cancer in mammals.

Abbreviations and Definitions

In accordance with the present invention and as used herein, the following abbreviations and terms are defined with the following meanings, unless explicitly stated otherwise. DSC: differential scanning calorimetry, XRPD: X-ray powder diffraction, NMR: nuclear magnetic resonance, API: active pharmaceutical ingredient; Vol: volume; mL: milliliter; g: gram; mg: milligram; 1H: proton; DMSO: dimethylsulphoxide; DMF: N,N-Dimethylformamide; KF: Karl Fischer; MC: moisture Content (% w/w); NA: not applicable; LR: lab reagent; μs: microsecond; mA: milliamps; kV: kilovolts; Hz: hertz; Mhz: megahertz; ° C.: degree Celsius; min: minute; % w/w: percent weight per weight.

In this specification and in the claims that follow, reference will be made to a number of terms that shall be defined to have the meanings below. All numerical designations, e.g., pH, temperature, time, concentration, and weight, including ranges, are approximations that typically may be varied (+) or (−) by increments of 0.1, 1.0, or 10.0, as appropriate. All numerical designations may be understood as preceded by the term "about". Reagents described herein are exemplary and equivalents of such may be known in the art.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "about" as used herein means variation one might see in measurements taken among different instruments, samples, and sample preparations. Such variation may include, for instance, colligative properties for thermal measurements. Typical variation among different x-ray diffractometers and sample preparations for crystalline solid forms is on the order of 0.2° 2θ. Typical variation for Raman and IR spectrometers is on the order of twice the resolution of the spectrometer. The resolution of the spectrometer used was about 2 cm$^{-1}$.

The term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

An "active agent" or "pharmaceutical" is a compound with a desired pharmacological effect. It includes all pharmaceutically acceptable forms of the active agent described. Unless explicitly stated otherwise, all embodiments of the invention may be practiced with any one or more different pharmaceutical salts of the active ingredients that has the desired effect. Reference to any drug or active agent in this disclosure includes any and all pharmaceutically compatible salts, solvates, and pharmaceutical compositions thereof that retain at least some of the physiological or chemotherapeutic effects of the drug itself, unless such isomers, salts, solvates, and/or compositions are explicitly excluded. Any such compound may be used as an alternative to the drug itself to improve efficacy, tolerability, delivery, or pharmacokinetics, or simply by choice within the good judgment of the manufacturer, distributor, pharmacist, clinician, or end user.

"Acute" in the context of cancers, refers to the relatively short time course in which cancer can become extremely serious and even lead to the death of a patient (e.g., they can be fatal in as little as a few weeks if left untreated) and differentiates them from "chronic" cancers, which may not have extremely debilitating effects on or lead to the death of a patient for many years.

"Administering" or "administration of a drug to a patient" (and grammatical equivalents of this phrase) refer both to direct administration, which may be administration to a patient by a medical professional or may be self-administration, as well as to indirect administration, which may be the act of prescribing a drug. For example, a physician who instructs a patient to self-administer a drug and/or provides a patient with a prescription for a drug is administering the drug to the patient.

A "chemotherapeutic agent" is a pharmaceutical compound that is given to a cancer patient primarily to eradicate, diminish, stabilize, or decrease the growth rate or metabolism of one or more malignant tumors in the patient. Included are agents such as carfilzomib or pomalidomide. The more general term "therapeutic agent" includes chemotherapeutics and radiation therapy.

The terms "dose" and "dosage" refer to a specific amount of active or therapeutic agent(s) for administration at one time. A "dosage form" is a physically discrete unit that has been packaged or provided as unitary dosages for subjects being treated. It contains a predetermined quantity of active agent calculated to produce the desired onset, tolerability, and therapeutic effect.

"Hypoxia-activated prodrug" refers to a drug that is less active or inactive under normoxia than under hypoxia or anoxia. Hypoxia-activated prodrugs include drugs that are activated by a variety of reducing agents and reductase enzymes, including without limitation single electron transferring enzymes (such as cytochrome P450 reductases) and two electron transferring (or hydride transferring) enzymes (see US Pat. App. Pub. Nos. 2005/0256191, 2007/0032455, and 2009/0136521, and PCT Pub. Nos. WO 2000/064864, WO 2004/087075, and WO 2007/002931, each of which is incorporated herein by reference). The hypoxia-activated prodrugs useful in the methods of the present invention are compounds of formula I, including but not limited to compounds where $Z_3$, as defined by that formula, is a 2-nitroimidazole moiety. Examples of particular hypoxia-activated prodrugs useful in the methods of the invention include without limitation TH-281, TH-302, and TH-308. Methods of synthesizing and formulating TH-302 and other compounds of formula I are described in PCT Pub. Nos. WO 2007/002931 and WO 2008/083101, each of which is incorporated herein by reference.

"Patient" or "subject" refers to mammals, particularly humans, but also to animals such as simians, cattle, horses, dogs, cats, and rodents suffering from blood cancer.

A "prodrug" is a compound that, after administration, is metabolized or otherwise converted to a biologically active or more active agent with respect to at least one beneficial property or effect.

"Relapsed or refractory" refers to a type of cancer that is resistant to treatment with an agent, or responds to treatment with an agent but comes back without being resistant to that agent, or responds to treatment with an agent but comes back resistant to that agent.

"Standard chemotherapy" refers to treatment with drugs in accordance with FDA labeling instructions and/or good clinical practice. Standard chemotherapy is well known to those of skill in the medical arts.

TH-302" refers to the compound N,N'-Bis(2-bromoethyl) phosphorodiamidic acid (1-methyl-2-nitro-1H-imidazol-5-yl)methyl ester having the formula:

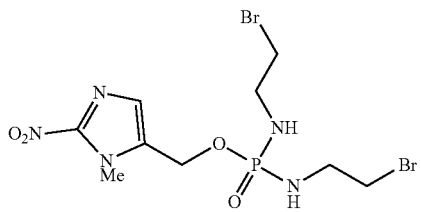 [SMILES: Cn1c(COP(=O)(NCCBr)NCCBr)cnc1[N+](=O)[O-]]

"Therapeutically effective amount" of a drug or an agent refers to an amount of drug or agent that, when administered to a patient with blood cancer, will have the intended therapeutic effect, e.g., alleviation, amelioration, palliation or elimination of one or more manifestations of the blood cancer in the patient. A therapeutic effect does not necessarily occur by administration of one dose and may occur only after administration of a series of therapeutically effective doses. Thus, a therapeutically effective amount may be administered in one or more administrations.

"Treating" or "treatment of" a condition or patient refers to taking steps to obtain beneficial or desired results, including clinical results. For purposes of this technology, beneficial or desired clinical results include, but are not limited to, alleviation or amelioration of one or more symptoms of blood cancer; diminishment of extent of disease; delay or slowing of disease progression; amelioration, palliation, or stabilization of the disease state; or other beneficial results.

This invention is based in part on the discovery that a hypoxia-activated prodrug such as TH-302 and carfilzomib or pomalidomide work especially well together in treating malignant conditions such as blood cancers, including but not limited to multiple myeloma. The two drug combinations of this invention (when administered in doses and on schedules adjusted for the particular animal model employed, relative to the human doses and schedules described herein) substantially inhibit cancer cell proliferation and increase survival in animal models of cancer and are expected to demonstrate similar benefit in human therapy. The benefit provided by the drug combinations of the invention will be, for many patients, more than that provided by any of the drugs alone and beyond what could be predicted. The present invention represents a significant advance in the treatment of this deadly disease.

In some patients, this two-drug combination provided by the invention may also be more tolerable to some patients than monotherapy. The use of the drug combinations described herein represents an important advance in cancer management and treatment.

The term "solvate" as used herein means a compound of the invention or a salt, thereof, that further includes a stoichiometric or non-stoichiometric amount of a solvent bound by non-covalent intermolecular forces in an amount of greater than about 0.3% when prepared according to the invention.

The term "hydrate" as used herein means a compound of the invention or a salt thereof, that further includes a stoichiometric or non-stoichiometric amount of water bound by non-covalent intermolecular forces. Hydrates are formed by the combination of one or more molecules of water with one of the substances in which the water retains its molecular state as $H_2O$, such combination being able to form one or more hydrate.

The term "anhydrous" as used herein means a compound of the invention or a salt thereof that contains less than about 3% by weight water or solvent when prepared according to the invention.

The term "drying" as used herein means a method of removing solvent and/or water from a compound of the invention which, unless otherwise specified, may be done at atmospheric pressure or under reduced pressure and with or without heating until the level of solvent and/or water contained reached an acceptable level.

The term "polymorphs" as used herein means crystal structures in which a compound can crystallize in different crystal packing arrangements, all of which have the same elemental composition. Different crystal forms usually have different X-ray diffraction patterns, infrared spectra, melting points/endotherm maximums, density hardness, crystal shape, optical and electrical properties, stability and solubility. Recrystallization solvent, rate of crystallization, storage temperature, and other factors may cause one crystal form to dominate.

The term "solid form" as used herein means crystal structures in which compounds can crystallize in different packing arrangements. Solid forms include polymorphs, hydrates, and solvates as those terms are used in this invention. Different solid forms, including different polymorphs, of the same compound exhibit different x-ray powder diffraction patterns and different spectra including infra-red, Raman, and solid-state NMR. Their optical, electrical, stability, and solubility properties may also differ.

The term "characterize" as used herein means to select data from an analytical measurement such as X-ray powder diffraction, infra-red spectroscopy, Raman spectroscopy, and/or solid-state NMR to distinguish one solid form of a compound from other solid forms of a compound.

The term "mammal" includes, without limitation, humans, domestic animals (e.g., dogs or cats), farm animals (cows, horses, or pigs), monkeys, rabbits, mice, and laboratory animals.

The term "pharmaceutically acceptable salt" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include those derived from inorganic bases such as sodium, potassium, lithium, ammonium, calcium, magnesium, iron, zinc, copper, manganese, aluminum salts and the like. Particularly preferred are the potassium and sodium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimetharnine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic nontoxic bases are isopropylamine, diethylamine, ethanolamine, trimethamine, dicyclohexylamine, choline, and caffeine. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19; Bundgaard, H., ed., *Design of Prodrugs* (Elsevier Science Publishers, Amsterdam 1985)). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

The compounds of the present invention which can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

As used herein, the term "condition" refers to a disease state for which the compounds, compositions and methods of the present invention are being used against.

Preparation of Compounds of the Invention

Scheme 1 illustrates a method of preparing TH-302.

Scheme 1: Process for the Preparation of TH-302

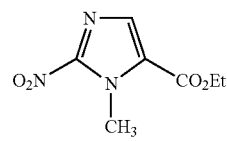

Imidazole carboxylic
acid ethyl ester (SM)
MW = 199.2

Step 1. Imidazole Carboxylic Acid

NaOH (RGT)
Purified water (SLV)
IPC: NMT 1.0 % SM by HPLC
HCl (RGT)
IPC: pH 1.0 ± 0.5
IPC: NMT 1.0% water by KF

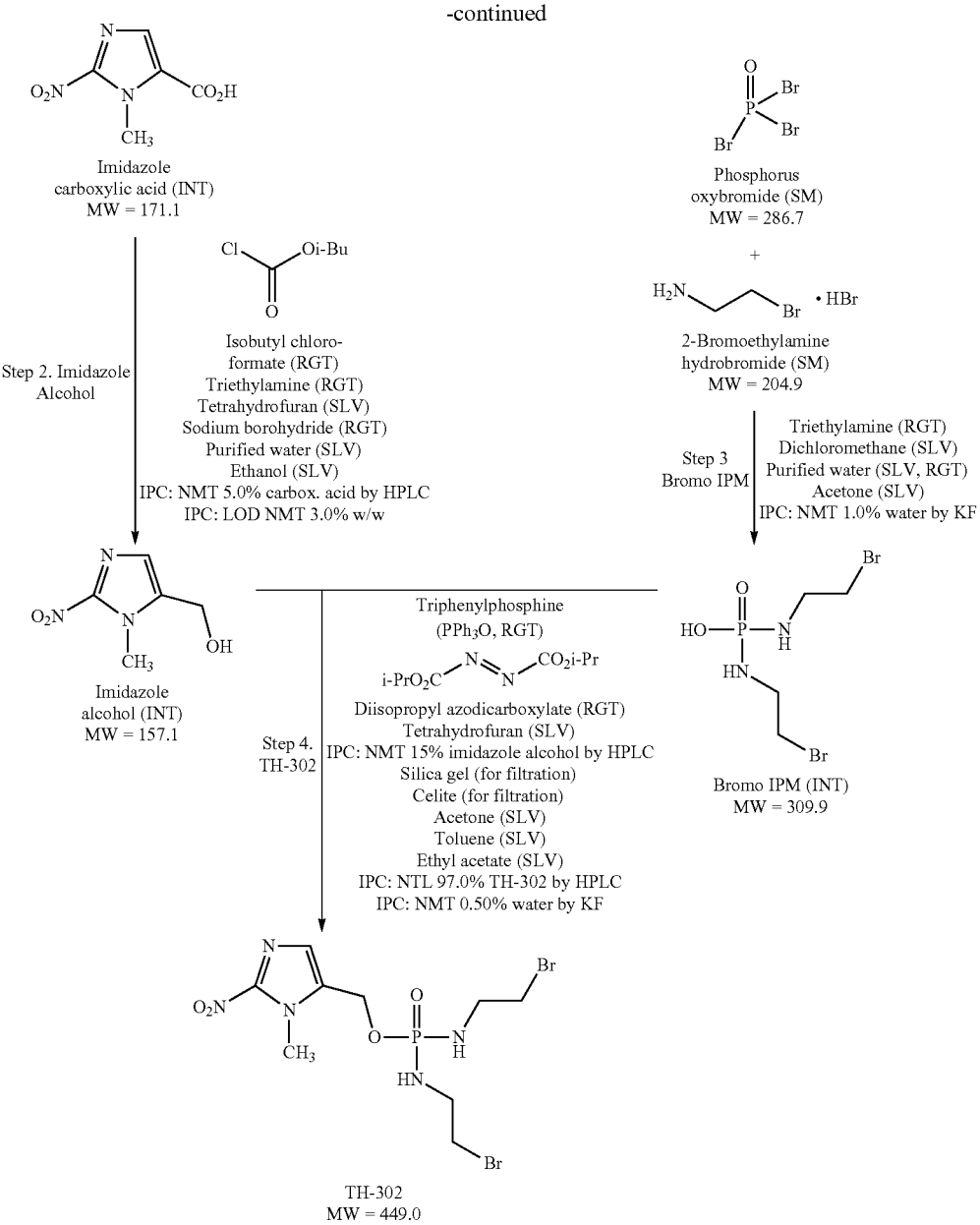

SM = Starting Material
MW = Molecular Weight
INT = Intermediate
LOD = Loss on drying
IPC = In-process Control
NMT = Not more than
RGT = Reagent
NLT = Not less than
SLV = Solvent TH-302 can be prepared by hydrolyzing (1-methyl-2-nitro-1H-imidazol-5-yl) ethyl ester above for example under aqueous conditions with a suitable base catalyst (e.g. NaOH in water at room temperature). The imidazole carboxylic acid prepared by this method can be used without further purification. However, it has been found that treating the dried crude intermediate product with a solvent such as acetonitrile, ethyl acetate, n-heptane, acetone, dimethylacetamide, dimethylformamide, 1, 4-dioxane, ethylene glycol, 2-propanol, 1-propanol, tetrahydrofuran (1:10 w/v) or combinations thereof in a vessel with heating, followed by cooling and filtration through a filtration aid with acetone decreased the number and levels of impurities in the product. The number and levels of impurities could be further reduced by treating the dried crude product with water (1:5.0 w/v) in a vessel with heating followed by cooling and filtration through a filtration aid with water.

The carboxylic acid of the imidazole can then be reduced using an excess of a suitable reducing agent (e.g. sodium borohydride in an appropriate solvent, typically aqueous. The reaction is exothermic (i.e. potentially explosive) releasing borane and hydrogen gases over several hours. It was determined that the oxygen balance of the product imidazole alcohol is about 106.9, which suggests a high propensity for rapid decomposition. It has been found that using NaOH, for example 0.01M NaOH followed by quenching the reaction with an acid. Non-limiting examples of acids include, but are not limited to water, acetic acid, hydrobromic acid, hydrochloric acid, sodium hydrogen phosphate, sulfuric acid, citric acid, carbonic acid, phosphoric acid, oxalic acid, boric acid and combinations thereof. In some embodiments, the acid may diluted with a solvent, such as water and/or tetrahydrofuran. In some embodiments, acetic acid or hydrochloric acid provide a better safety profile, presumably because it is easier to control the temperature during the addition of the reducing agent and the excess reducing agent is destroyed after the reaction is complete. This also results in improved yields and fewer impurities, presumably due to reduced impurities from the reducing agent and decomposition of the product. Using this process, greater than 98.5% purity could be achieved for this intermediate. The formation of ether linkage can be accomplished by treating the product imidazole alcohol with solution of N,N'-Bis(2-bromoethyl)phosphorodiamidic acid (Bromo IPM), a trisubstituted phosphine and diisopropyl azodicarboxylate in tetrahydrofuran at room temperature to afford TH-302. It has been found that by recrystallizing the product from a solvents listed in the examples, one could avoid further purification by column chromatography, which allowed for both reduced solvent use especially on larger scales.

Scheme 2 illustrates an alternative method of preparing TH-302.

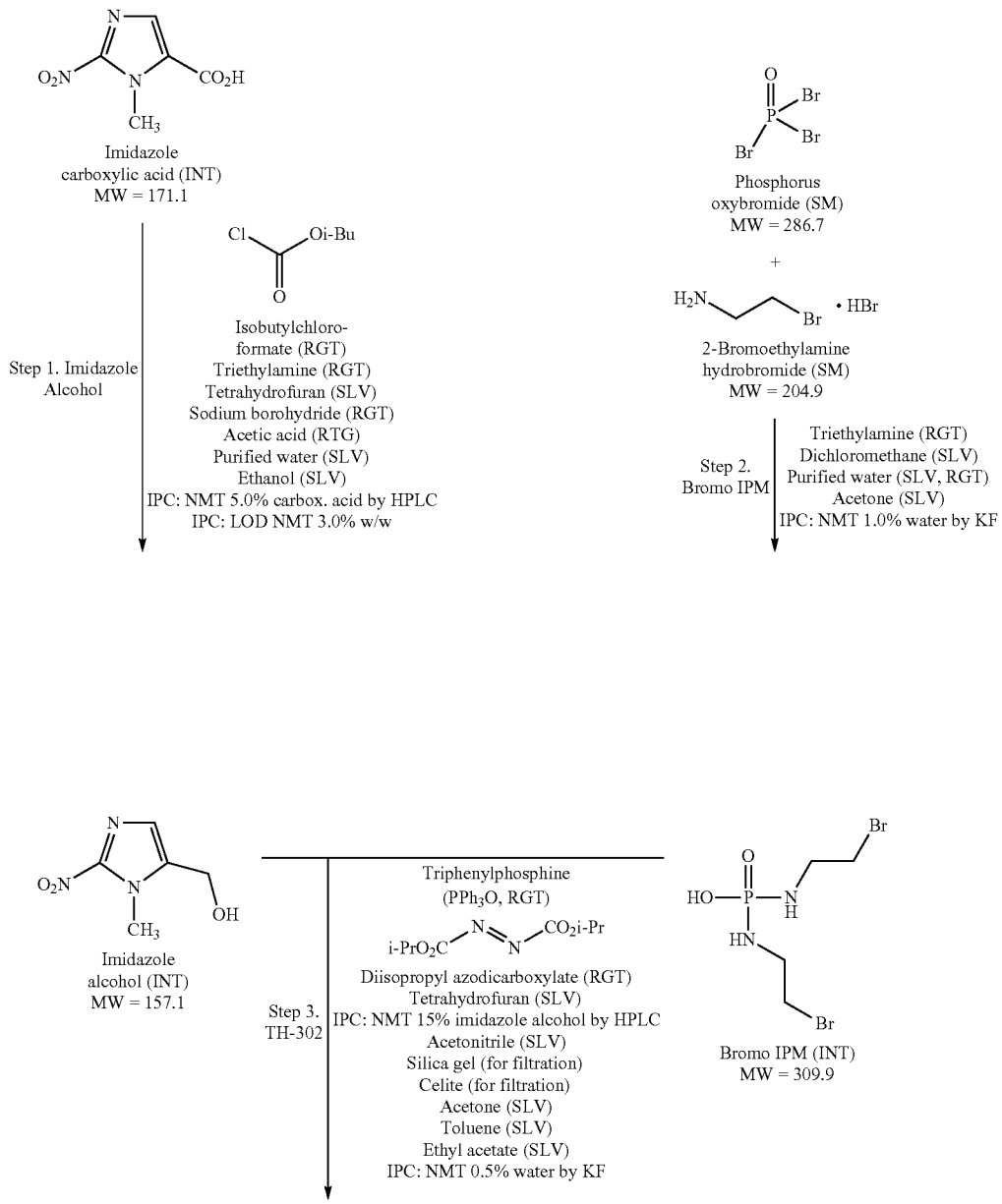

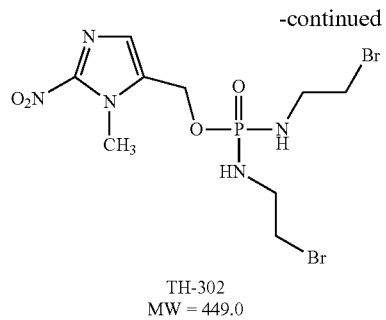

TH-302
MW = 449.0

SM = Starting Material
MW = Molecular Weight
INT = Intermediate
LOD = Loss on drying
IPC = In-process Control
NMT = Not more than
RGT = Reagent
NLT = Not less than
SLV = Solvent The intermediate Br-IPM can be prepared by treating phosphorous oxybromide with 2-bromoethylamine in the presence of a base, such as triethylamine, in an inert solvent, such as dichloromethane, at an appropriate temperature, typically at room temperature. Keeping the water content in the solvent below 0.02% w/v provided Br-IPM in higher yields.

Unless otherwise specified, the compounds disclosed herein may be isolated using typical isolation and purification techniques known in the art, including, for example, chromatographic and recrystallization methods.

According to the invention, TH-302 may be further treated to form pharmaceutically acceptable salts. Treatment of a compound of the invention with an acid or base may form, respectively, a pharmaceutically acceptable acid addition salt and a pharmaceutically acceptable base addition salt, each as defined above. Various inorganic and organic acids and bases known in the art including those defined herein may be used to effect the conversion to the salt.

The invention also provides pharmaceutically hydrates, and solvates of TH-302. For example, while some compounds are provided herein as anhydrous having no molecules of water per molecule of TH-302, the present invention also provides compounds that are monohydrates, trihydrates, sesquihydrates, and the like.

The term "prodrug" refers to a pharmacologically inactive derivative of a parent drug molecule that requires biotransformation, either spontaneous or enzymatic, within the organism to release the active drug.

Crystalline Solid Embodiments of the Invention and their Preparation

The present invention also provides crystalline solid forms of TH-302 and processes for their preparation and pharmaceutical compositions comprising these forms.

In developing a process for production of an active pharmaceutical ingredient (API), two factors are of great importance: the impurity profile and the crystal morphology of the compound. Preferably the API has levels of impurities below 0.2% and is in the most thermodynamically stable crystalline solid form. The isolation and crystallization work indicated that there was at least one crystalline solid form TH-302 (designated as Form A).

The solid form of the invention may be described by one or more of several techniques including X-ray powder diffraction, Raman spectroscopy, IR spectroscopy, and thermal methods. Further, combinations of such techniques may be used to describe the invention. For example, one or more X-ray powder diffraction peaks combined with one or more Raman peaks may be used to describe one or more solid forms of the invention in a way that differentiates it from the other solid forms.

Although it characterizes a form, it is not necessary to rely only upon an entire diffraction pattern or spectrum to characterize a solid form. Those of ordinary skill in the pharmaceutical arts recognize that a subset of a diffraction pattern or spectrum may be used to characterize a solid form provided that subset distinguishes the solid form from the other forms being characterized. Thus, one or more X-ray powder diffraction peaks alone may be used to characterize a solid form. Likewise, one or more IR peaks alone or Raman peaks alone may be used to characterize a solid form. Such characterizations are done by comparing the X-ray, Raman, and IR data amongst the forms to determine characteristic peaks.

One may also combine data from other techniques in such a characterization. Thus, one may rely upon one or more peaks from an x-ray powder diffraction and for example, Raman or IR data, to characterize a form. For example, if one or more x-ray peaks characterize a form, one could also consider Raman or IR data to characterize the form. It is sometimes helpful to consider Raman data, for example, in pharmaceutical formulations.

Figure 3:
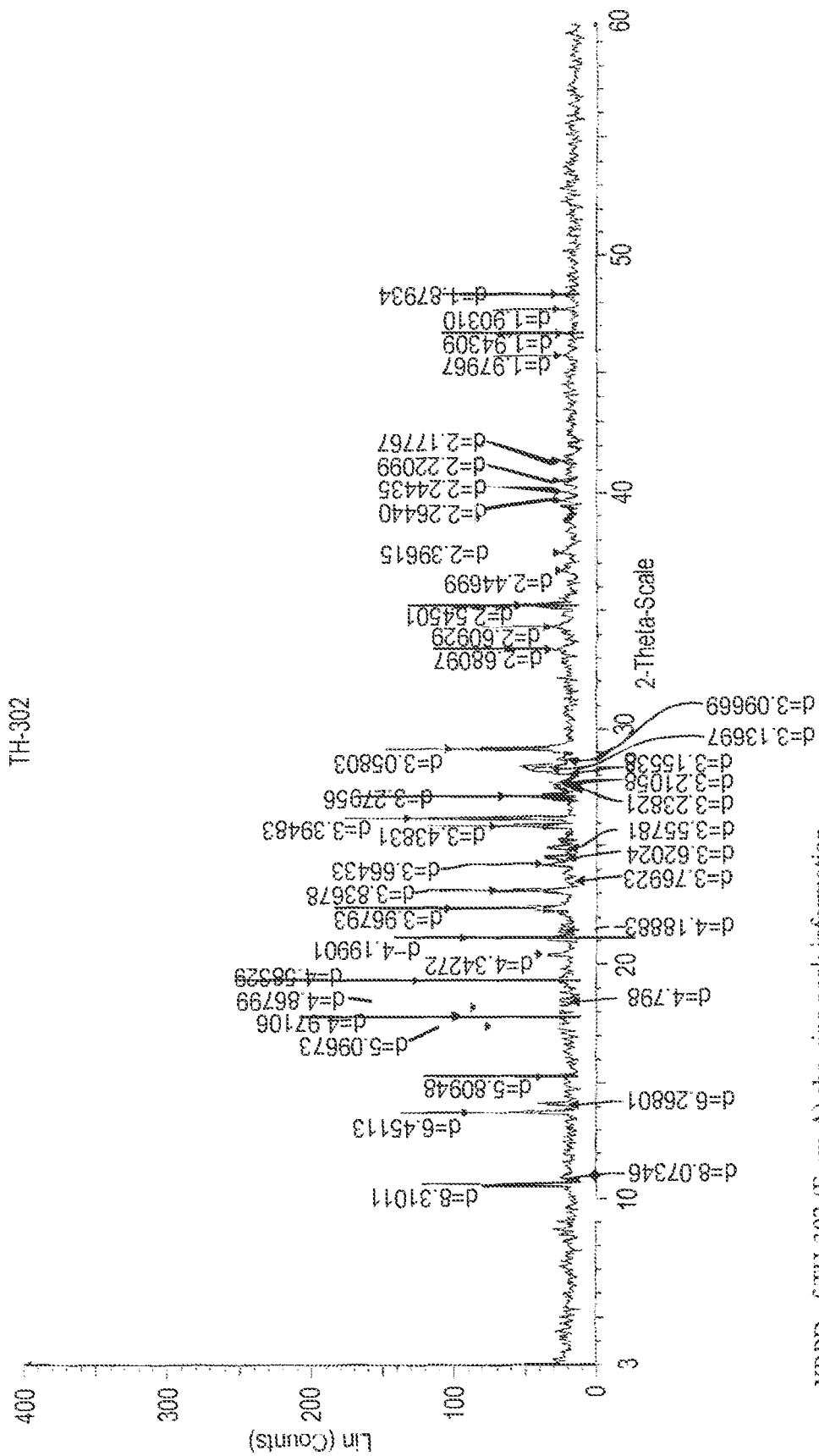
FIG. 3 shows an XRPD of crystalline solid form A of TH-302 showing peak information.

The polymorphs were identified from by using different crystallization conditions as noted in the Examples below. FIGS. 1 and 3 respectively show the DSC trace and the X-ray powder pattern for the crystalline solid. Differential scanning calorimetry (DSC) of Form A of TH-302 defined by an onset temperature at 98.06° C. In the DSC trace, the sharpness of the completion of melt at about 100.06° C. is characteristic.

In the X-ray powder diffraction pattern, the peaks at about 9.5 and 25.5 are the main features of the pattern (for a discussion of the theory of X-ray powder diffraction patterns see "X-ray diffraction procedures" by H. P. Klug and L. E. Alexander, J. Wiley, New York (1974)). The peaks at about 19.3° 2θ and 26.2° 2θ characterize Form A. Because the typical variation in any given x-ray powder diffraction peak is on the order of 0.2° 2θ, when selecting peaks to characterize a polymorph, one selects the most intense peaks or those that are at least twice that value (i.e., 0.4° θ) from a peak from another polymorph. Thus, in a particular polymorph x-ray pattern, a peak that is at least 0.4° θ from a peak in another polymorph is eligible to be considered as a peak that can either alone or together with another peak be used to characterize that polymorph. FIG. 4 identifies the main peaks of Form A.

Preferred orientation can affect peak intensities, but not peak positions, in XRPD patterns. Preferred orientation causes some peaks in this region to be diminished (or increased). Crystal habit does not clearly differentiate between the solid forms; a variety of habits have been observed for each form, including needles, blades, plates, and irregular-shaped particles.

Thus in one embodiment, the present invention provides TH-302 in new crystalline form designated as Form A.

Thus in one embodiment, the invention provides TH-302 in a crystalline solid form, including a substantially pure form, which provides at least one of:
(i) an X-ray powder diffraction pattern substantially in accordance with FIG. 3; and
(iii) a DSC scan substantially in accordance with FIG. 1 and
(iii) an infra red spectrum substantially in accordance with FIG. 5;
herein designated as Form A.

In another embodiment, the invention provides TH-302 in a crystalline solid form, including a substantially pure form, which provides an X-ray powder diffraction pattern comprising peaks at about 19.3 and about 26.2° 2θ herein designated as Form A.

In another embodiment, the invention provides TH-302 in a crystalline solid form, including a substantially pure form, which provides a DSC endotherm maximum of about 100° C.; herein designated as Form A.

In another embodiment, the invention provides TH-302 in a crystalline solid form, including a substantially pure form, which provides an infra-red spectrum comprising absorption peaks at about 2966 and 1352 $cm^{-1}$.

In another embodiment, the invention provides a crystalline polymorph of [4-(6-fluoro-7-methylamino-2,4-dioxo-1, 4-dihydro-2H-quinazolin-3-yl)-phenyl]-5-chloro-thiophen-2-yl-sulfonylurea potassium salt which provides an infra red spectrum containing absorption peaks at about 3024, 2966, 1554, 1542, 1435, 1413, 1376, 1352, 1275, 1248, 1187, 1172, 1127, 1014, 971, 826, 808, 698, 659, 578, 566, 254 $cm^{-1}$; herein designated as Form A In another embodiment, the invention provides a crystalline polymorph of TH-302 which provides spectrum containing at least one, but fewer than the above peak listings, herein designated as Form A.

Crystalline form A of TH-302 is anhydrous which is stable to 15% relative humidity (RH) at 25° C. No change in the chemical purity of TH-302 was observed after one week when in accelerated stability tests at high temperature (40° C.) and high relative humidity (75% RH). An improvement in the physical appearance of a dosage form of a drug enhances both physician and patient acceptance and increases the likelihood of success of the treatment.

Any of the analytical techniques described herein may be used to detect the presence of the solid forms in such compositions. Detection may be done qualitatively, quantitatively, or semi-quantitatively as those terms as used and understood by those of skill in the solid-state analytical arts.

For these analyses, use of standard analytical techniques involving reference standards may be used. Further, such methods may include use of techniques such as partial-lease squares in conjunction with a diffractive or spectroscopic analytical technique. These techniques may also be used in pharmaceutical compositions of the invention.

Preparation of Crystalline Solid Forms of the Invention

Furthermore, the present invention is directed to processes for the preparation of crystalline solid forms of TH-302.

Crystalline solid forms of TH-302 may be prepared by various methods as outlined below. Other well-known crystallization procedures as well as modification of the procedures outline above may be utilized.

In another embodiment of the present invention there is provided TH-302 in a crystalline solid form A, which is obtained by:
(i) crystallizing TH-302 from at least one solvent selected from the group consisting of ethyl acetate, ethanol, t-butanol, acetonitrile, dichloromethane, acetone, nitromethane, chloroform, isopropyl alcohol, n-butanol, n-propanol, water, toluene, n-heptane, methyl t-butyl ether, isopropyl acetate, diisopropyl ether, t-butanol, N,N-dimethylacetamide, dimethylsulfoxide, trifluroethanol, tetrahydrofuran.

Furthermore, the present invention is directed to the above described processes for the preparation of crystalline solid forms of TH-302.

TH-302 in a crystalline solid or amorphous form may be prepared by various methods as further described below in the Examples. The examples illustrate, but do not limit the scope of the present invention. TH-302 in crystalline solid forms may be isolated using typical isolation and purification techniques known in the art, including, for example, chromatographic, recrystallization and other crystallization procedures as well as modification of the procedures outlined above.

Pharmaceutical Formulations

A "medicament combination" as used herein refers to two or more medications that are used in combination and may be co-formulated (admixed together) or separately formulated (not admixed or otherwise combined together in a single unit dose form).

Formulations of TH-302 suitable for iv injection and methods for administering them in the treatment of cancer that are suitable for use in practice of the present invention are described in PCT Pub. Nos. WO 07/002931, WO 08/083101, and WO 10/048330, incorporated herein by reference. Suitable formulations of these drugs for oral administration are described in WO 12/142520, incorporated herein by reference.

While the various methods of the invention are illustrated specifically with TH-302 other particular compounds of Formula I, as well as other formulations, and dosing schedules of the invention, can be assessed for safety and efficacy in preclinical models and clinical trials. In such studies, one uses a compound, formulation, or drug combination of the invention in a preclinical animal model, for example, a homograft or allograft model using tumor cell lines derived from the same species, or a xenograft of human tumor cells in an immune-compromised animal, or in a human clinical trial approved by the appropriate regulatory authority. Using such systems and models, the investigator may determine, for example, the maximum tolerable dose and the dose required for a significant beneficial therapeutic effect using such models.

Depending on efficacy and side effect profile, a TH-302 and another drug may be distributed and administered separately in a treatment of a particular disease or condition. Thus, in accordance with the invention, TH-302 may be combined with another drug for administration together; or the drugs may be separately formulated and administered.

The invention also encompasses various combinations of agents for marketing or distribution together. Such combinations are optionally marketed and distributed in kit form. The combinations or kits may comprise separate packs of an effective amount of a TH-302; and another drug. The combination or kit will be suitably packaged and may also contain or be marketed in combination with written instructions that direct the clinician on the use of the combination or elements of the kit for chemotherapy in accordance with the invention.

Treatment Methods and Uses

In one aspect, the present invention provides a method of treating a blood cancer comprising administering a therapeutically effective amount of TH-302 alone or in combination with another ant-cancer agent. TH-302 is administered in a therapeutically effective amount to a patient in need of such treatment, thereby treating the cancer.

In suitable embodiments, combinations of another anti-cancer agent and TH-302 are administered to a patient, separately, sequentially, or simultaneously, for the treatment of the cancer. When administered in combination with another anti-cancer agent in one embodiment, TH-302 is administered before administering the other anti-cancer agent.

In various embodiments, a method of the invention is employed as a first, second, third or later line of treatment. As used herein, a "first line" or "second line" or "third line" of treatment refers to a place in the order of treatment with different medications or other therapies received by a patient. First line therapy regimens are treatments given first, whereas second or third line therapy are given after the first line therapy or after the second line therapy, respectively. Therefore, first line therapy is "the first treatment for a disease or condition." In patients with cancer, first line therapy, sometimes referred to as "primary therapy" or "primary treatment", can be surgery, chemotherapy, radiation therapy, or a combination of these therapies. Typically, a patient is given a subsequent chemotherapy regimen (second or third line therapy), either because the patient did not show a positive clinical or showed only a sub-clinical response to a first or second line therapy or showed a positive clinical response but later experienced a relapse, sometimes with disease now resistant to the earlier therapy that elicited the earlier positive response.

Methods of preparation of and pharmaceutical compositions of TH-302, and other methods of treating cancer by administering TH-302 are described in Duan et al., J. Med. Chem. 2008, 51, 2412-2420 PCT Pub. Nos. WO 2007/002931, WO 2008/083101, and WO 2010/048330, each of which is incorporated herein by reference. Other methods of treating cancers, which may be used in combination with the methods of the present invention, are known to one of skilled in the art, and are described, for example, in the product descriptions found in the 2010 or more current edition of the Physician's Desk Reference, Medical Economics Company, Inc., Oradell, N.J.; Goodman and Gilman's The pharmacological basis of therapeutics., Eds. Hardman et al., McGraw-Hill. N.Y. (US) 2011, 12th Ed., and in publications of the U.S. Food and Drug Administration and the NCCN Guidelines (National Comprehensive Cancer Network). Such described and known methods can be appropriately modified by one of skill in the art, in view of this disclosure, to practice the treatment methods of the present technology.

It should be understood that the foregoing discussion, embodiments and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The following preparations and examples are given to enable those skilled in the art to more clearly understand and to practice the present invention. They should not be considered as limiting the scope of the invention, but merely as being illustrative and representative thereof.

EXAMPLES

General Methods

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

Example 1: Synthesis of TH-302

Step 1—Preparation Intermediate Imidazole Carboxylic Acid:

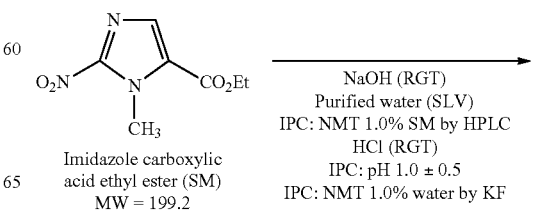

Imidazole carboxylic acid ethyl ester (SM)
MW = 199.2

NaOH (RGT)
Purified water (SLV)
IPC: NMT 1.0% SM by HPLC
HCl (RGT)
IPC: pH 1.0 ± 0.5
IPC: NMT 1.0% water by KF

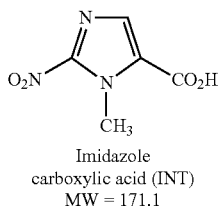

Imidazole
carboxylic acid (INT)
MW = 171.1

Crude imidazole carboxylic acid ethyl ester (1:1.0 w/w) was taken in water (1:10.0 w/v) at 25±5° C. and cooled to 17±3° C. A 2.5 N sodium hydroxide solution (10 V) was added slowly at 17±3° C. The reaction mass was warmed to 25±5° C. and monitored by HPLC. After the completion of reaction, the reaction mass was cooled to 3±2° C. and pH of the reaction mass adjusted to 1±0.5 using 6 M HCl at 3±2° C. The reaction mass was then warmed to 25±5° C. and extracted with ethyl acetate (3×10 V). The combined organic layers were washed with water (1×10 V) followed by brine (1×10 V). The organic layer was dried over sodium sulfate (3 w/w), filtered over Celite and concentrated. n-Heptane (1.0 w/v) was added and the the reaction mixture was concentrated below 45° C. to 2.0 w/v. The reaction mass was cooled to 0±5° C. The solid was filtered, and the bed was washed with n-heptane (1×0.5 w/v) and dried at 35±5° C. In a vessel, acetone (1:10 w/v) was added. Dry crude imidazole carboxylic acid (ICA) from 1.12 was added to the acetone. The mixture was warmed to 45±5° C. and was stirred for 30 minutes. The mass was cooled to 28±3° C. and filtered through a Celite bed. The filter bed was washed with 1:1.0 w/v of acetone. Water (1:5.0 w/v) was added to the filtrate and the mixture was concentrated. The concentrated mass was cooled to 5±5° C. and stirred for 30 minutes. The material was filtered and the solid was washed 2×1:1.0 w/v of water at 3±2° C. The product was dried for 2 hours at 25±5° C. and then at 45±5° C. As can be seen below, the number and levels of impurities are decreased.

TABLE 1

Purity and Impurity Profile Comparison of Typical Crude ICA and Purified ICA

| Compound | Structure | Crude ICA Assay (% w/w) | Purified ICA Assay (% w/w) |
| --- | --- | --- | --- |
| ICA | | 95.0 | 98.6 |
| TH-2716 | 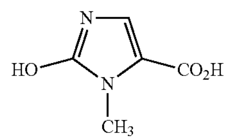 | 0.52 | ND |
| TH-2827 | 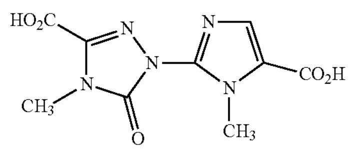 [SMILES: Cn1c(C(=O)O)cnc1-n1nc(C(=O)O)n(C)c1=O] | 0.23 | ND |
| TH-2796 | 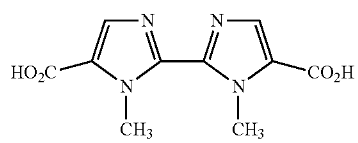 | 0.26 | 0.05 |
| TH-2717 | 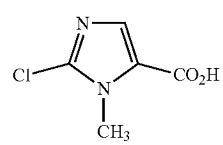 | 0.08 | 0.14 |
| TH-2810 | 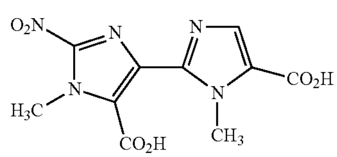 [SMILES: Cn1c(C(=O)O)cnc1-c1nc([N+](=O)[O-])n(C)c1C(=O)O] | 0.32 | ND |
| TH-2795 | 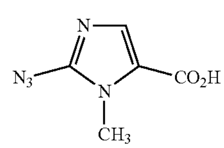 | 0.52 | 0.10 |
| ICAEE | | 0.10 | ND |
| Total Impurities | | 2.5 | 0.29 |

Step 2—Imidazole Alcohol:

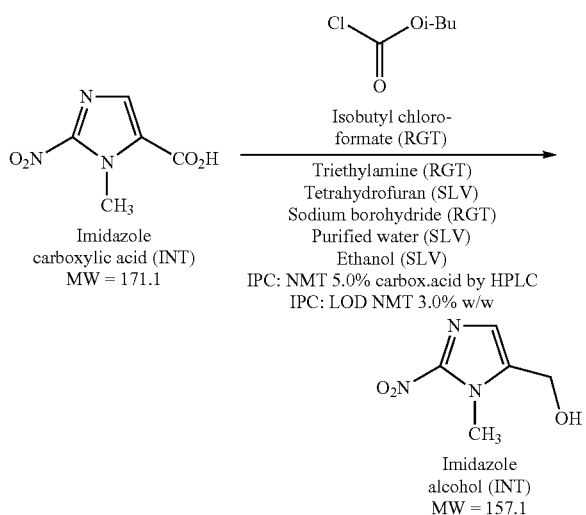

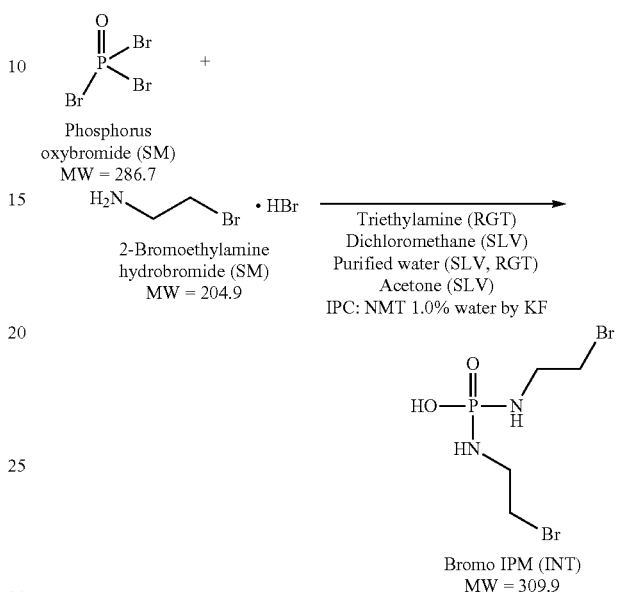

Imidazole carboxylic acid (1.0 w/w) was taken in tetrahydrofuran (10 w/v) under nitrogen atmosphere at 25±5° C. The reaction mass was cooled to −15±5° C. Triethylamine (1:1.23 w/v) was added slowly over a period of 1 hour maintaining the temperature at −15±5° C. The reaction mass was stirred at −15±5° C. for 15-20 min. Isobutylchloroformate (1:1.14 w/v) was added slowly over a period of 1 hour maintaining the temperature at −15±5° C. The reaction mass was stirred at −15±5° C. for 30-40 min. A solution of sodium borohydride (1:1.15 w/w) in 0.01M aqueous sodium hydroxide (2.2 w/v) was divided into 6 lots and added to the above reaction mass while maintaining the temperature of the reaction mass between 0±10° C. for 40-60 min for each lot. The reaction mass was warmed to 25±5° C. and stirred until imidazole carboxylic acid content <5.0% w/w. The reaction mass was filtered and the bed was washed with tetrahydrofuran (1:2.5 w/v). The filtrate was quenched with 10% acetic acid in water at 25±5° C. Reaction mass stirred for 50-60 minutes at 25±5° C. The filtrate was concentrated below 45° C. until no distillate was observed. The mass was cooled to 5±5° C. and stirred for 50-60 minutes. The reaction mass was filtered and the solid was taken in ethanol (1:0.53 w/v). The reaction mass was cooled 0±5° C. and stirred for 30-40 min. The solid was filtered and the bed was washed ethanol (1:0.13 w/v). The solid was dried at 40±5° C.

Step 3—Synthesis of Intermediate Br-IPM:

2-Bromoethylamine hydrobromide (1:1.0 w/w) and POBr$_3$ (1:0.7 w/w) were taken in DCM (1:2 w/v) under nitrogen atmosphere. The reaction mixture was cooled to −70±5° C. Triethylamine (1:1.36 w/v) in DCM (1:5 w/v) was added to the reaction mass at −70±5° C. The reaction mass was stirred for additional 30 min at −70±5° C. Reaction mass was warmed to 0±3° C. and water (1:1.72 w/v) was added. The reaction mixture was stirred at 0±3° C. for 4 hrs. The solid obtained was filtered and filter cake was washed with ice cold water (2 ×1:0.86 w/v) and then with chilled acetone (2×1:0.86 w/v). The solid was dried in at 20±5° C.

Step 4 Synthesis of TH-302:

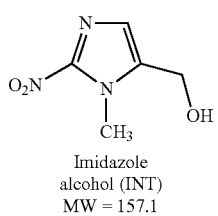

Imidazole alcohol (INT)
MW = 157.1

Triphenylphosphine (PPh$_3$O, RGT)

i-PrO$_2$C—N=N—CO$_2$i-Pr

Diisopropyl azodicarboxylate (RGT)
Tetrahydrofuran (SLV)
IPC: NMT 15% imidazole alcohol by HPLC
Silica gel (for filtration)
Celite (for filtration)
Acetone (SLV)
Toluene (SLV)
Ethyl acetate (SLV)
IPC: NTL 97.0% TH-302 by HPLC
IPC: NMT 0.50% water by KF

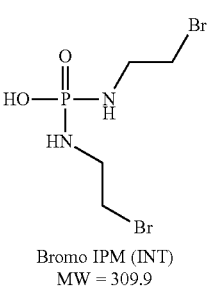

Bromo IPM (INT)
MW = 309.9

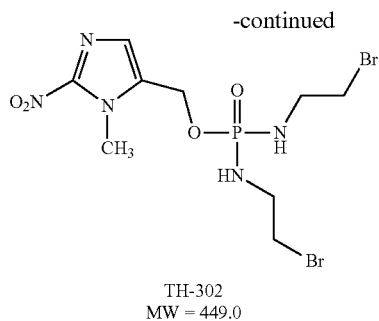

TH-302
MW = 449.0

Imidazole alcohol (IA) (1:1.0 w/w), Bromo-IPM (1:2.26 w/w) and triphenylphosphine (1:2.0 w/w) were added to THF (1:13.5 w/v) at 25±5° C. The reaction mass was cooled to 0±5° C. and DIAD (1.5 w/v) was added. The reaction mixture warmed to 25±5° C. and stirred for 2 hours. Progress of the reaction was monitored by HPLC. Solvent was removed below 50° C. under vacuum. Solvent exchange with acetonitrile (1:10.0 w/v) below 50° C. was performed. The syrupy liquid was re-dissolved in acetonitrile (1:10.0 w/v) and the mixture was stirred at −20±5° C. for 1 hour. The resulting solid was filtered and the filtrate bed was washed with chilled acetonitrile (1:1.0 w/v). The acetonitrile filtrate was concentrated below 50° C. under vacuum. The concentrated mass was re-dissolved in ethyl acetate (1:10.0 w/v) and concentrated below 50° C. under vacuum. The ethyl acetate strip off was repeated two more times. Ethyl acetate (1:10.0 w/v) and silica gel (230-400 mesh, 1:5.3 w/w) were added to the concentrated reaction mass. The mixture was concentrated below 40° C. under vacuum. n-Heptane (1:5.0 w/v) was charged to the above mass and the mixture was evaporated below 40° C. under vacuum. n-Heptane (1:5.0 w/v) was again added to the above mass and the solid was filtered and the bed was washed with n-heptane (1:1.0 w/v). The solid was suspended in a mixture of toluene (1:7.1 w/v) and n-heptane (1:21.3 w/v), stirred at 35±5° C. for 15-20 minutes, filtered off and the bed was washed with n-heptane (1:1.0 w/v). The solid was re-suspended in a mixture of toluene (1:10.6 w/v) and n-heptane (1:10.6 w/v), stirred at 35±5° C. for 15-20 minutes, filtered off and the bed was washed with n-heptane (1:1.0 w/v). The solid was suspended in acetone (1:19.0 w/v), stirred at 35±5° C. for 15-20 minutes, filtered off and the bed was washed with acetone (1:1.0 w/v). The acetone washes were repeated 3 more times. Filtrates from the above acetone washings were combined and concentrated below 40° C. under vacuum. The residue dissolved in ethyl acetate (1:10.0 w/v) and concentrated below 40° C. under vacuum. The ethyl acetate strip off was repeated one more time. The residue was re-dissolved in ethyl acetate (1:5.5 w/v), cooled to 0±3° C. and stirred at 0±3° C. for 2 h and then at −20±5° C. for 2 h. The solid was filtered and the solid was washed with ethyl acetate (1:0.10 w/v). The solid was dissolved in ethyl acetate (1:10.0 w/v) at 50±5° C. and the resulting solution was filtered through a cartridge filter. The filtrate was concentrated to ~4.0 w/w and stirred at 0±3° C. for 4 hours. The solid was filtered and washed with ethyl acetate (1:0.10 w/v). The crystallization from ethyl acetate was repeated and TH-302 was dried at 25±5° C. Table 2 shows how the process reduces solvent use.

TABLE 2

Solvent and Silica Gel Usage for 10 kg Column and 10 kg Column-free Purification

| Consumables | Column Process[a] | Column-free Process[b] |
|---|---|---|
| Silica Gel | 460 kg | 62 kg |
| Acetonitrile | NA | 290 L |
| n-Heptane | NA | 530 L |
| Ethyl acetate | 800 L | 680 L |
| Toluene | 9000 L | 210 L |
| Acetone | 5600 L | 870 L |

[a]Amounts are estimated from a 5 kg batch
[b]Amounts are estimated

Example 2: Synthesis of TH-302 Using Alternative Procedure to Purify ICA

Crude ICA was prepared according to the method described in Example 1. In a vessel, water (1:7.0 w/v) was added. Dry crude ICA was added to the water. The reaction mixture was heated to 85±5° C. until a clear solution was obtained. The reaction mass was cooled to 20±5° C. and filtered through a Celite bed. The filter bed was washed with 2×5.0 V of n-heptane. The material was dried for 2 hours at 25±5° C. and then 45±5° C. As can be seen below, the number and levels of impurities decreased.

TABLE 3

Purity and Impurity Profile Comparison of Typical Crude ICA and Purified ICA

| Compound | Crude ICA Assay (% w/w) | Purified ICA Assay (% w/w) |
|---|---|---|
| ICA | 96.6 | 99.5 |
| TH-2716 | 0.34 | 0.05 |
| TH-2827 | 0.40 | ND |
| TH-2796 | 0.29 | ND |
| TH-2717 | 0.29 | 0.24 |
| TH-2810 | 0.56 | ND |
| TH-2795 | 0.54 | ND |
| ICAEE | 0.13 | ND |
| Total Impurities | 2.6 | 0.38 |

Example 3: Synthesis of TH-302 Using Alternative Procedure to Purify ICA

Crude ICA was prepared according to the method described in Example 1. In a vessel ethanol (1:30.0 w/v) and ICA (1:1.0 w/w) were mixed. The reaction mixture was stirred at 25±5° C. for 30 minutes and filtered. Water (1:50.0 w/v) was added and the mixture was stirred at 50±5° C. for 30 minutes. The reaction mass was cooled to 20±5° C. and filtered. The isolated solid was dried at 25±5° C. for 24 hours. As can be seen below, the number and levels of impurities generally decreased.

TABLE 4

Purity and Impurity Profile Comparison of Typical Crude ICA and Purified ICA

| Compound | Crude ICA Assay (% w/w) | Purified ICA Assay (% w/w) |
|---|---|---|
| ICA | 92.6 | 97.9 |
| TH-2716 | 4.81 | 0.13 |
| TH-2827 | ND | ND |
| TH-2796 | 1.39 | 0.50 |
| TH-2717 | 0.98 | 1.25 |
| TH-2810 | ND | ND |
| TH-2795 | ND | ND |
| ICAEE | ND | ND |
| Total Impurities | 7.8 | 0.38 |

Example 4: Synthesis of TH-302 Using Alternative Procedure to Purify ICA

Crude ICA was prepared according to the method described in Example 1. In a vessel acetonitrile (1:20.0 w/v) and ICA (1:1.0 w/w) were mixed at 25±5° C. for one hour. The reaction mixture was filtered and the solution was concentrated to ~6 volumes. The mixture was then cooled to 0±5° C., stirred at this temperature for one hour and filtered. The isolated solid was dried at 25±5° C. for 24 hours. As can be seen below the number of impurities decreased and except for TH-2717, the amounts also decreased.

TABLE 5

Purity and Impurity Profile Comparison of Typical Crude ICA and Purified ICA

| Compound | Crude ICA Assay (% w/w) | Purified ICA Assay (% w/w) |
|---|---|---|
| ICA | 92.6 | 98.6 |
| TH-2716 | 4.81 | ND |
| TH-2827 | ND | ND |
| TH-2796 | 1.39 | ND |
| TH-2717 | 0.98 | 1.21 |
| TH-2810 | ND | ND |
| TH-2795 | ND | ND |
| ICAEE | ND | ND |
| Total Impurities | 7.8 | 1.2. |

Example 5: Synthesis of TH-302 Using Alternative Procedure to Purify ICA

Crude ICA is prepared according to the method described in Example 1 and purified by treatment with dimethylacetamide and water.

Example 6: Synthesis of TH-302 Using Alternative Procedure to Purify ICA

Crude ICA is prepared according to the method described in Example 1 and purified by treatment with dimethylformamide and water.

Example 7: Synthesis of TH-302 Using Alternative Procedure to Purify ICA

Crude ICA is prepared according to the method described in Example 1 and purified by crystallization from a 1,4-dioxane and water mixture.

Example 8: Synthesis of TH-302 Using Alternative Procedure to Purify ICA

Crude ICA is prepared according to the method described in Example 1 and purified by crystallization from a mixture of ethylene glycol and water.

Example 9: Synthesis of TH-302 Using Alternative Procedure to Purify ICA

Crude ICA is prepared according to the method described in Example 1 and purified by treatment with 2-propanol and water.

Example 10: Synthesis of TH-302 Using Alternative Procedure to Purify ICA

Crude ICA is prepared according to the method described in Example 1 and purified by treatment with 1-propanol and water.

Example 11: Synthesis of TH-302 Using Alternative Procedure to Purify ICA

Crude ICA is prepared according to the method described in Example 1 and purified by crystallization from a mixture of tetrahydrofuran and water.

Example 12: Synthesis of TH-302 Using Alternative Procedure to Quench IA

The reduction of ICA to IA was carried out according to Example 1 except that after reaction completion and filtration of the inorganics, the filtrate was quenched with 1.5 M hydrochloric acid.

Example 13: Synthesis of TH-302 Using Alternative Procedure to Quench IA

The reduction of ICA to IA was carried out according to Example 1 except that after reaction completion and filtration of the inorganics, the filtrate was quenched with 1.5 M hydrobromic acid.

Example 14: Synthesis of TH-302 Using Alternative Procedure to Quench IA

The reduction of ICA to IA was carried out according to Example 1 except that after reaction completion and filtration of the inorganics, the filtrate was quenched with hydrobromic acid in acetic acid.

Example 15: Synthesis of TH-302 Using Alternative Procedure to Quench IA

The reduction of ICA to IA was carried out according to Example 1 except that after reaction completion and filtration of the inorganics, the filtrate was treated with sodium hydrogen phosphate.

Example 16: Synthesis of TH-302 Using Alternative Procedure to Quench IA

The reduction of ICA to IA was carried out according to Example 1 except that after reaction completion and filtration of the inorganics, the filtrate was quenched with 10% acetic acid in tetrahydrofuran.

Example 17: Synthesis of TH-302 Using Alternative Procedure to Quench IA

The reduction of ICA to IA was carried out according to Example 1 except that after reaction completion and filtration of the inorganics, the filtrate was quenched with water.

Example 18: Synthesis of TH-302 Using Alternative Procedure to Quench IA

The reduction of ICA to IA is carried out according to Example 1 except that after reaction completion and filtration of the inorganics, the filtrate is quenched with sulfuric acid.

Example 19: Synthesis of TH-302 Using Alternative Procedure to Quench IA

The reduction of ICA to IA is carried out according to Example 1 except that after reaction completion and filtration of the inorganics, the filtrate is quenched with citric acid.

Example 20: Synthesis of TH-302 Using Alternative Procedure to Quench IA

The reduction of ICA to IA is carried out according to Example 1 except that after reaction completion and filtration of the inorganics, the filtrate is treated with carbonic acid.

Example 21: Synthesis of TH-302 Using Alternative Procedure to Quench IA

The reduction of ICA to IA is carried out according to Example 1 except that after reaction completion and filtration of the inorganics, the filtrate is treated with phosphoric acid.

Example 22: Synthesis of TH-302 Using Alternative Procedure to Quench IA

The reduction of ICA to IA is carried out according to Example 1 except that after reaction completion and filtration of the inorganics, the filtrate is quenched with oxalic acid.

Example 23: Synthesis of TH-302 Using Alternative Procedure to Quench IA

The reduction of ICA to IA is carried out according to Example 1 except that after reaction completion and filtration of the inorganics, the filtrate is quenched with boric acid.

Example 24: Synthesis of TH-302 Using Alternative Procedure to Purify TH-302

Coupling of bromo-IPM and IA was performed according to Example 1 except that after concentration of the reaction mixture, ethyl acetate (1:10 w/v) was added to the concentrated mass. The mixture was stirred at −55±5° C. for 2 hours. The resulting solid was filtered and washed with chilled EtOAc (1:2.0 w/v). The solid was reslurried in ethyl acetate (1:10 w/v) at −55±5° C. for 2 hours, filtered and the solid was washed with chilled ethyl acetate (1:1.0 w/v). The filtrates from both filtrations were combined and treated with silica gel (1:5.3 w/w) of silica gel (230-400 mesh). The mixture was concentrated below 40° C. under vacuum. n-Heptane (1:5.0 w/v) was again added to the above mass and the solid was filtered and the bed was washed with n-heptane (1:1.0 w/v). The solid was suspended in a mixture of toluene (1:7.1 w/v) and n-heptane (1:21.3 w/v), stirred at 35±5° C. for 15-20 minutes, filtered off and the bed was washed with n-heptane (1:1.0 w/v). The solid was resuspended in a mixture of toluene (1:10.6 w/v) and n-heptane (1:10.6 w/v), stirred at 35±5° C. for 15-20 minutes, filtered off and the bed was washed with n-heptane (1:1.0 w/v). The solid was suspended in acetone (1:19.0 w/v), stirred at 35±5° C. for 15-20 minutes, filtered off and the bed was washed with acetone (1:1.0 w/v). The acetone washes were repeated 3 more times. Filtrates from the above acetone washings were combined and concentrated below 40° C. under vacuum. The residue dissolved in ethyl acetate (1:5.5 w/v), cooled to 0±3° C. and stirred at 0±3° C. for 2 h and then at −20±5° C. for 2 h. The solid was filtered and the solid was washed with ethyl acetate (1:0.10 w/v). The solid was dissolved in ethyl acetate (1:27 w/v), stirred at 50±5° C. and filtered through Celite. The filtrate was concentrated to ~4.0 w/w and stirred at 0±5° C. for 4 hours. The recrystallization from ethyl acetate was repeated and TH-302 was dried at 25±5° C. Table 4 shows how the process reduced solvent use.

TABLE 4

Estimated Solvent and Silica Gel Usage for Column and 10 kg Column-free (EtOAc) Purification

| Consumables | Column Process | Column-free Process |
|---|---|---|
| Silica Gel | 460 kg | 62 kg |
| n-Heptane | NA | 530 L |
| Ethyl acetate | 800 L | 970 L |
| Toluene | 9000 L | 210 L |
| Acetone | 5600 L | 870 L |

Example 26: Preparation of Polymorph Form A by Recrystallization

Recrystallization: A sample of TH-302 was used for crystallization experiments from various solvents noted below to characterize solid forms of TH-302. A saturated solution was prepared in a test tube or round bottom flask and then crystallizations were performed. Crystallization methods included slow cooling of a hot saturated solution prepared at ~45° C. The test tube was sealed and insulated to perform slow crystallization. Precipitation experiments were performed by adding anti solvents quickly. In solvents where TH-302 did not readily dissolve, the TH-302 was recovered by filtration from the slurry. The isolated solids were dried at 40° C. under vacuum and were initially characterized by DSC further analyzed by $^1$H-NMR to check for degradation or solvation. Recrystallizations were scaled-up and the solids were re-characterized by DSC and $^1$H-NMR and further characterized by XRPD. If crystallization was not observed, the experiment was repeated and crystallization was attempted by addition of an anti-solvent. If the sample crystallized, the following analytical techniques were performed.

Instrumental for Solid Forms

Differential Scanning Calorimetry (DSC)

Instrumentation and Equipment (as Listed or Equivalent)

| Instrument | TA Instruments Q2000 differential scanning calorimetry modules. |
|---|---|
| Data acquisition | Computer capable of running TA Instruments and TA Advantage thermal analysis software |
| Sample pans | T-zero aluminium pan (open) |

Instrument Parameters

| Nitrogen flow rate | 30 mL/min |
|---|---|
| Initial temperature | 25° C. |
| Heating rate | 10° C./min |
| Final temperature | 250° C. |

Sample Preparation and Reporting

Samples were accurately weighed between 2.0-5.0 mg into a previously tared aluminium pan (open). The weight was entered in the DSC experimental setup. The above steps were repeated for a reference pan without any sample. The onset temperature and peak temperature values for TH-302 form A are noted below and in FIG. 1.

| DSC (° C.) | |
|---|---|
| Onset | Peak |
| 98.06 | 100.06 |

XRPD (X-Ray Powder Diffraction)

Bruker AXS C2 GADDS Diffractometer

This method used a Bruker D8 advance system applicable for the determination of the x-ray diffraction of TH-302.

Instrumentation and Equipment (as Listed or Equivalent)

| Instrument | Bruker D8 Advance |
|---|---|
| Detector | Scintillation Detector |
| Data acquisition | An electronic data acquisition system was used |

Scan Parameters

| Scan type | Locked Coupled |
|---|---|
| Scan mode | Continuous |
| Scan axis (2 theta) | Start: 3.000°, Stop: 60.000° |
| Scan step size (2 theta) | 0.03° |
| Scan time per step | 0.5 second |
| Delay time | 0 second |

Motorized Slits

| Divergence slit | 0.300° |
|---|---|
| Anti scattering slit | 0.300° |
| Sample rotation | Sychron rotation in "On" condition |

Generator

| Voltage | 40 kV |
|---|---|
| Current | 30 mA |

Sample Preparation and Results

An appropriate quantity of sample was placed in a sample holder and pressed using the glass slides. The sample holder was wiped to avoid any spillage on the instrument. The above parameters were set in the instrument. A blank was generated by scanning the empty sample holder. The sample was scanned and the blank correction performed and the pattern of diffractogram was reported. FIG. 3 shows an XRPD of crystalline solid form A of TH-302 showing peak information and FIG. 4 shows XRPD peak information for crystalline solid form A of TH-302.

$^1$H NMR Identification

Figure 2:
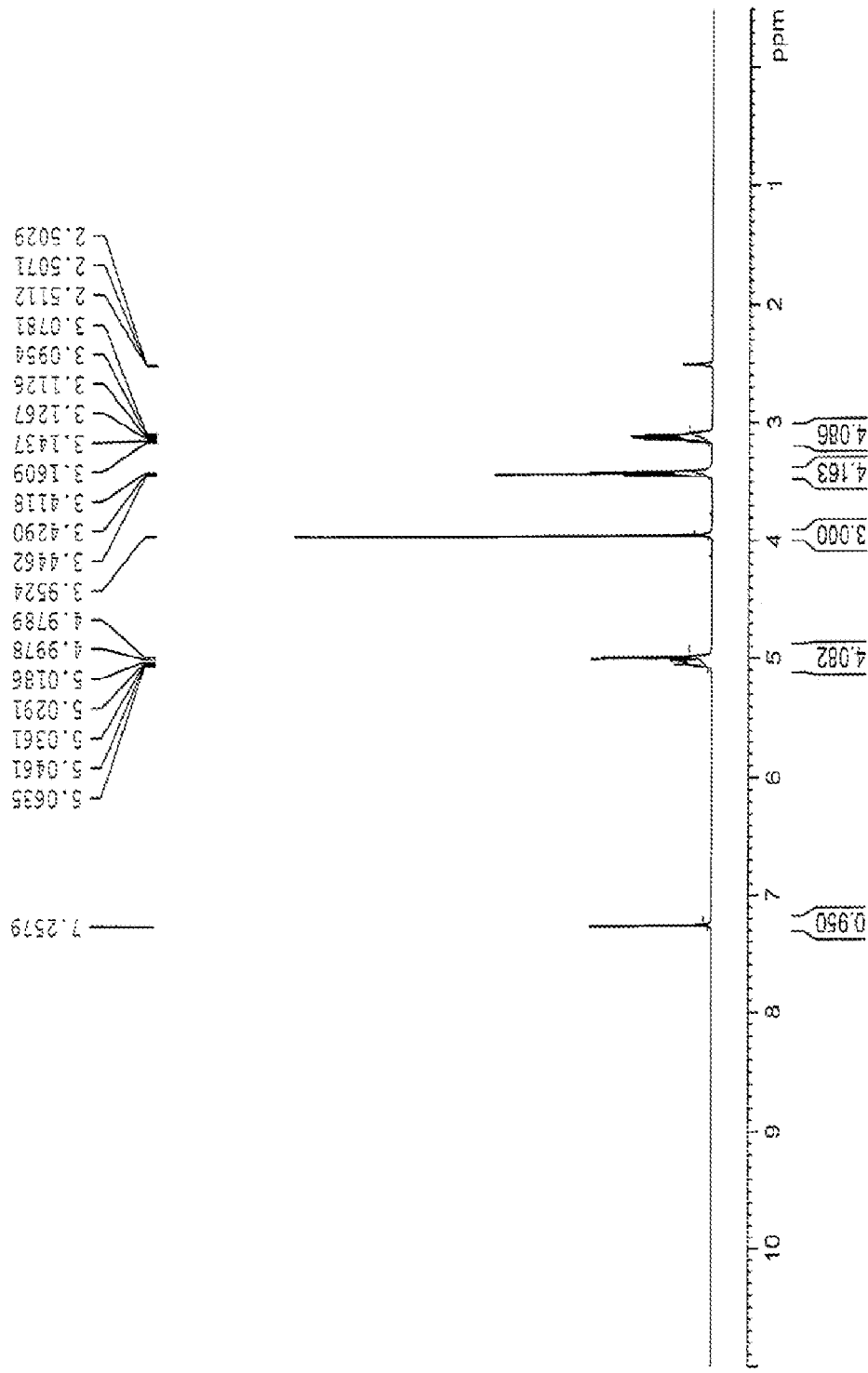
FIG. 2 shows the $^1$H-NMR of crystalline solid form A of TH-302.

Spectra were collected on a Bruker Advance 300/400 MHz equipped with auto sampler. Samples were prepared in $d_6$-DMSO. FIG. 2 shows the $^1$H-NMR of crystalline solid form A of TH-302.

Raman Spectroscopy

Figure 5:
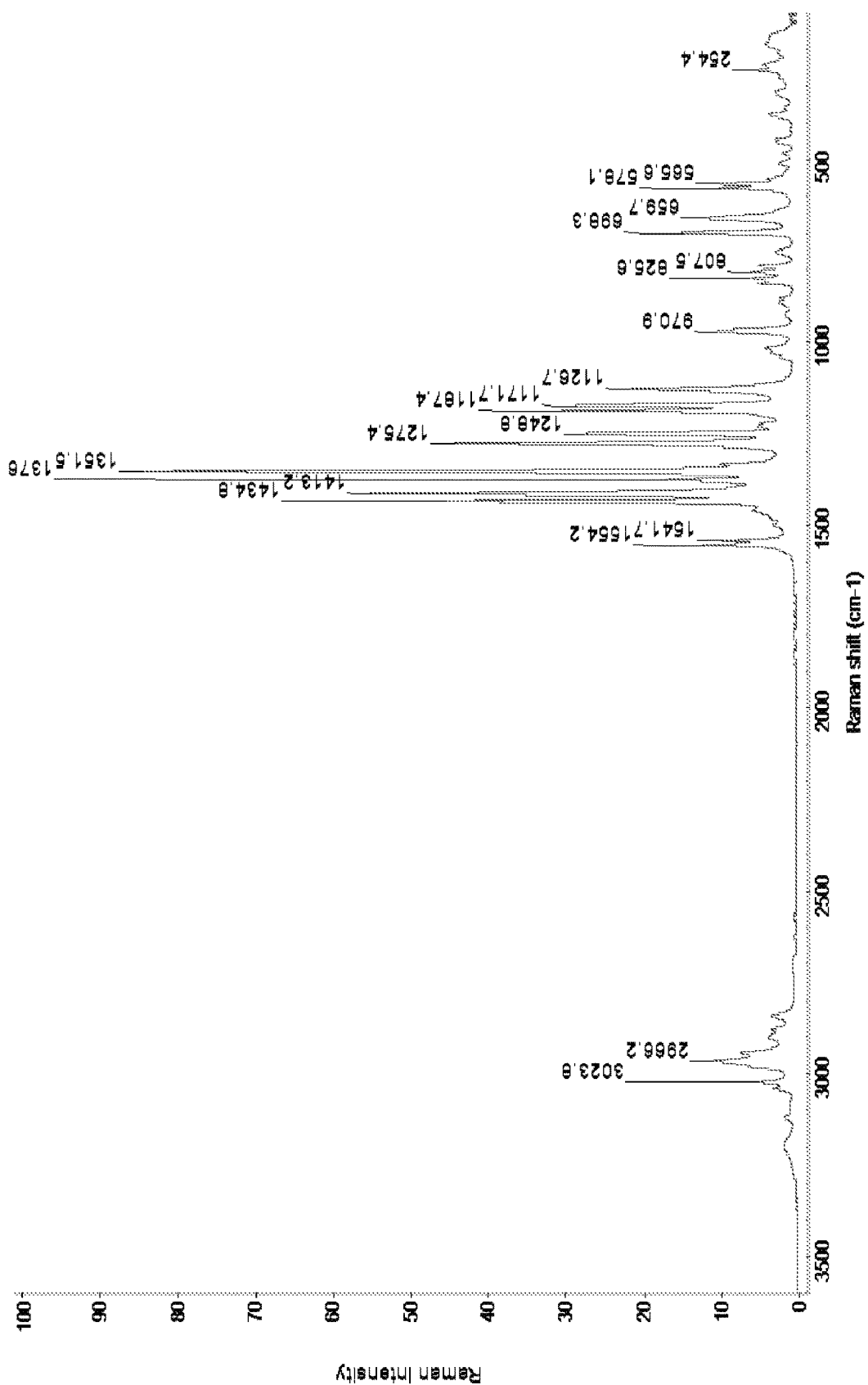
FIG. 5 shows the Raman Spectra of TH-302 (Form A)

Raman spectra were acquired on a FT-Raman NXR accessory module interfaced to a Nexus 670 spectrometer (Thermo Nicolet) equipped with a InGaAs detector. Wavelength verification was performed using sulfur and cyclohexane. Each sample was prepared for analysis by placing the sample into a pellet holder. Approximately 0.508 W of Nd:YVO4 laser power (1064 nm excitation wavelength) was used to irradiate the sample. Each spectrum represents 256 co-added scans collected at a spectral resolution of 4 cm-1. Raman spectra of TH-302 is shown in FIG. 5. FIG. 5 was generated using OMNIC v7.2 software. The spectra show peak locations and peak intensity ratios.

Experiments Using Single Solvents.

Results of attempts to recrystallize TH-302 from various solvents and characterization of solids obtained are reported below. Solvent quantities are reported on a v/w basis relative to TH-302.

| Solvent | Remarks |
|---|---|
| Ethanol (2 v) | Crystallization, DSC complies. |
| Ethanol (2v) | Crystallization, DSC &XRPD comply. |
| Ethyl acetate (8 v) | Crystallization, DSC complies |
| t-Butanol (5v) | Crystallization, DSC complies. |
| t-Butanol (5 v) | Crystallization, DSC & XRPD comply. |
| Acetonitrile (<3 v) | Part. Concentration & Crystallization, DSC complies |
| Dichloromethane (7 v) | Crystallization, DSC complies |
| Acetone (<6 v) | Part. Concentration & Crystallization, DSC complies |
| Nitromethane (<1 v) | Crystallization, DSC complies |
| Chloroform (<2 v) | Crystallization, DSC complies |
| Isopropyl alcohol (6 v) | Crystallization, DSC complies |
| n-Butanol (4 v) | Crystallization, DSC complies |
| n-Propanol (4 v) | Crystallization, DSC complies |
| Water (25 v) | Crystallization (dissolved at 50° C.), DSC & XRPD comply, MC: 0.15% (KF) |
| Water (10 v) | Slurry experiment, DSC complies |
| Toluene (10 v) | Slurry experiment, DSC complies |
| n-Heptane (10 v) | Slurry experiment, DSC complies |
| Methyl t-butyl ether (10 v) | Slurry experiment, DSC complies |
| Isopropyl acetate (10 v) | Slurry experiment, DSC complies |
| Diisopropyl ether (10 v) | Slurry experiment, DSC complies |
| t-Butanol (5 v) | Lyophilisation, DSC complies |

Experiments Using Anti Solvents.

Results of attempts to recrystallize TH-302 from various solvent mixtures and characterization of solids obtained are reported below. Solvent quantities are reported on a v/w basis relative to TH-302.

| Solvent-1 | Solvent-2 (Anti solvent) | Remarks |
|---|---|---|
| N,N-Dimethylacetamide (3v) | Water(5v) | Crystallization, DSC complies |
| Acetone (6v) | Water (20v) | Crystallization, DSC complies |
| Acetone (6v) | n-Heptane (20v) | Crystallization, DSC complies |
| Acetonitrile (5v) | Water (20v) | Crystallization, DSC complies. |
| Acetonitrile (5v) | Water (20v) | Crystallization, DSC and XRPD comply. MC: 0.13% (KF) |
| Dimethylsulphoxide (2v) | Water (2v) | Crystallization, DSC complies |
| Dimethylsulphoxide (2v) | Water (2v) | Crystallization, DSC and XRPD comply. MC: 0.1% (KF) |
| Methanol (2v) | Methyl t-butyl ether (8v) | Crystallization, DSC complies |
| Trifluoroethanol (1v) | Diisopropyl ether (2v) | Crystallization, DSC complies |
| Trifluoroethanol (1v) | Methyl-t-butyl ether (4v) | Crystallization, DSC complies |
| Tetrahydrofuran (5v) | Diisopropyl ether (5v) | Crystallization, DSC complies |
| Tetrahydrofuran (5v) | Methyl t-butyl ether (6v) | Crystallization, DSC complies |
| Tetrahydrofuran (5v) | n-Heptane (8v) | Crystallization, DSC complies |
| N,N-Dimethylformamide (1v) | Water (2v) | Crystallization, DSC complies |
| N,N-Dimethylformamide (1v) | Water (2v) | Crystallization, DSC and XRPD comply. MC: .07% (KF) |

All the solids isolated from various crystallizations had very similar DSC thermograms which were consistent with TH-302 form A as characterized herein. The differences in onset and peak values were not considered significant as these were due to normal experimental variations, and thus no indication of different polymorphs other than Form A. This has been confirmed by XRPD using solvents of particular interest like Ethanol, t-Butanol, water, mixtures of Acetonitrile-water, DMSO-water and DMF-water. There was no evidence of solvation as determined by NMR. A stoichiometric hydrate of TH-302, 1:1 water: TH-302 on a molar basis, would have 3.87% water on a % w/w basis. Samples obtained from aqueous solvents were analyzed by KF, and showed no more than 0.15% w/w water by KF, thus providing no significant indication of hydration.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

What is claimed is:

1. A process for preparing a compound of Formula V:

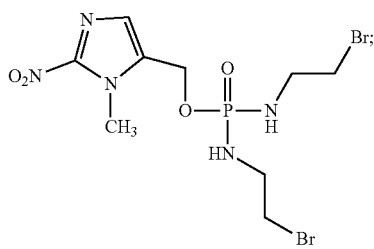

Formula V comprising reacting a compound of Formula II with a reducing agent in a base followed by adding an acid to provide a compound of Formula III:

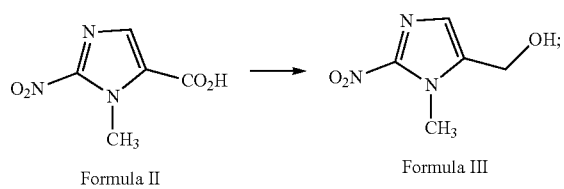

and reacting a compound of Formula III with a trisubstituted phosphine, an oxidizing agent and a phosphorus containing compound having the formula IV:

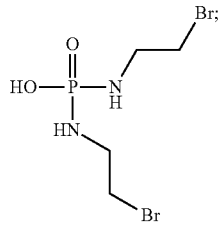

Formula IV to provide a compound of Formula V.

2. The process of claim 1, further comprising purifying the compound of Formula V;
the process comprising filtering the compound through a solid filtration aid with a solvent selected from the group consisting of acetonitrile, ethyl acetate, n-heptane, acetone, dimethylacetamide, dimethylformamide, 1,4-dioxane, ethylene glycol, 2-propanol, 1-propanol, tetrahydrofuran.

3. The process of claim 2 wherein the solvent is acetonitrile.

4. The process of claim 1, further comprising purifying the compound of Formula V;
comprising recrystallizing the compound of formula V from ethyl acetate.

5. The process of claim 1, wherein the reducing agent is sodium borohydride.

6. The process of claim 5, wherein the base is NaOH.

7. The process of claim 1, wherein the acid is selected from the group consisting of water, acetic acid, hydrobromic acid, hydrochloric acid, sodium hydrogen phosphate, sulfuric acid, citric acid, carbonic acid, phosphoric acid, oxalic acid, boric acid and combinations thereof.

8. The process of claim 7, wherein the acid is acetic acid.

9. The process of claim 1, wherein the trisubstituted phosphine is triphenyl phosphine.

10. The process of claim 1, wherein the oxidizing agent is diisopropyl azodicarboxylate.

11. The method of claim 6, wherein the ratio of the compound of formula II to sodium borohydride is about 1:1.1 to about 1:1.5 and the concentration of NaOH is from about 0.01 M to about 0.05 M.

12. The process of claim 2, wherein the solid filtration aid is diatomaceous earth.

13. The process of claim 1, wherein the compound of formula IV is prepared by reacting $POBr_3$ with 2-bromoethylamine, or a salt thereof in a solvent wherein the water content is not more than about 0.02% v/v.

14. The process of claim 13, further comprising converting the compound of formula IV to a compound of Formula V.

15. The process of claim 1, wherein the compound of Formula II is prepared by:
reacting a compound of Formula I; wherein R is a $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur, each of which is optionally substituted;
with a compound of formula MOH, wherein M is selected from the group consisting of Na and K; to form a compound of Formula II:

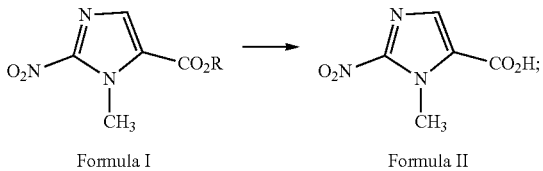

Formula I          Formula II and
purifying the compound of Formula II by filtering the compound through a solid filtration aid; with a solvent selected from the group consisting of water, acetonitrile, ethyl acetate, n-heptane, acetone, dimethylacetamide, dimethylformamide, 1, 4-dioxane, ethylene glycol, 2-propanol, 1-propanol, tetrahydrofuran and combinations thereof.

16. The process of claim 15, wherein R in Formula I is ethyl.

17. The process of claim 15, wherein M in MOH is Na.

18. The process of claim 15, wherein the solid filtration aid is diatomaceous earth.

* * * * *